(12) United States Patent
Lattner et al.

(10) Patent No.: US 7,256,318 B2
(45) Date of Patent: Aug. 14, 2007

(54) REGENERATION TEMPERATURE CONTROL IN A CATALYTIC REACTION SYSTEM

(75) Inventors: James R. Lattner, Seabrook, TX (US); Keith Holroyd Kuechler, Friendswood, TX (US); Nicolas P. Coute, Houston, TX (US); Paul N. Chisholm, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 583 days.

(21) Appl. No.: 10/403,270

(22) Filed: Mar. 28, 2003

(65) Prior Publication Data

US 2004/0192993 A1    Sep. 30, 2004

(51) Int. Cl.
*C07C 1/00* (2006.01)
*B01J 38/12* (2006.01)

(52) U.S. Cl. .................. 585/640; 585/639; 502/38
(58) Field of Classification Search ........ 585/638–640; 502/38
See application file for complete search history.

(56) References Cited

U.S. PATENT DOCUMENTS

| | | | |
|---|---|---|---|
| 4,861,739 A | 8/1989 | Pellet et al. | 502/64 |
| 4,873,390 A | 10/1989 | Lewis et al. | 585/638 |
| 5,002,915 A | 3/1991 | Harandi et al. | 502/51 |
| 5,914,433 A | 6/1999 | Marker | 585/313 |
| 5,997,728 A | 12/1999 | Adewuyi et al. | 208/120.01 |
| 6,023,005 A | 2/2000 | Lattner et al. | 585/639 |
| 6,039,863 A | 3/2000 | Palmas | 208/113 |
| 6,045,688 A | 4/2000 | Ruotto | 208/113 |
| 6,106,697 A | 8/2000 | Swan et al. | 208/77 |
| 6,245,703 B1 * | 6/2001 | Kuechler et al. | 502/22 |
| 6,437,208 B1 * | 8/2002 | Kuechler et al. | 585/640 |
| 6,455,747 B1 * | 9/2002 | Lattner et al. | 585/638 |
| 6,825,391 B2 | 11/2004 | Janssen et al. | 585/640 |

FOREIGN PATENT DOCUMENTS

WO    WO 01/85871 A1 * 11/2001

* cited by examiner

*Primary Examiner*—Glenn Caldarola
*Assistant Examiner*—In Suk Bullock

(57) ABSTRACT

This invention is directed to controlling regenerator temperature in an oxygenate to olefin process. Because a significant amount of heat can produced in the regenerator during the regeneration process, at least a portion of the heat must be removed to keep the system from getting too hot. This invention removes heat during the regeneration of the catalyst, using appropriate circulation of catalyst between the reactor and the regenerator. Sufficient circulation can eliminate the need for the use of a catalyst cooler in the regeneration system.

41 Claims, 1 Drawing Sheet

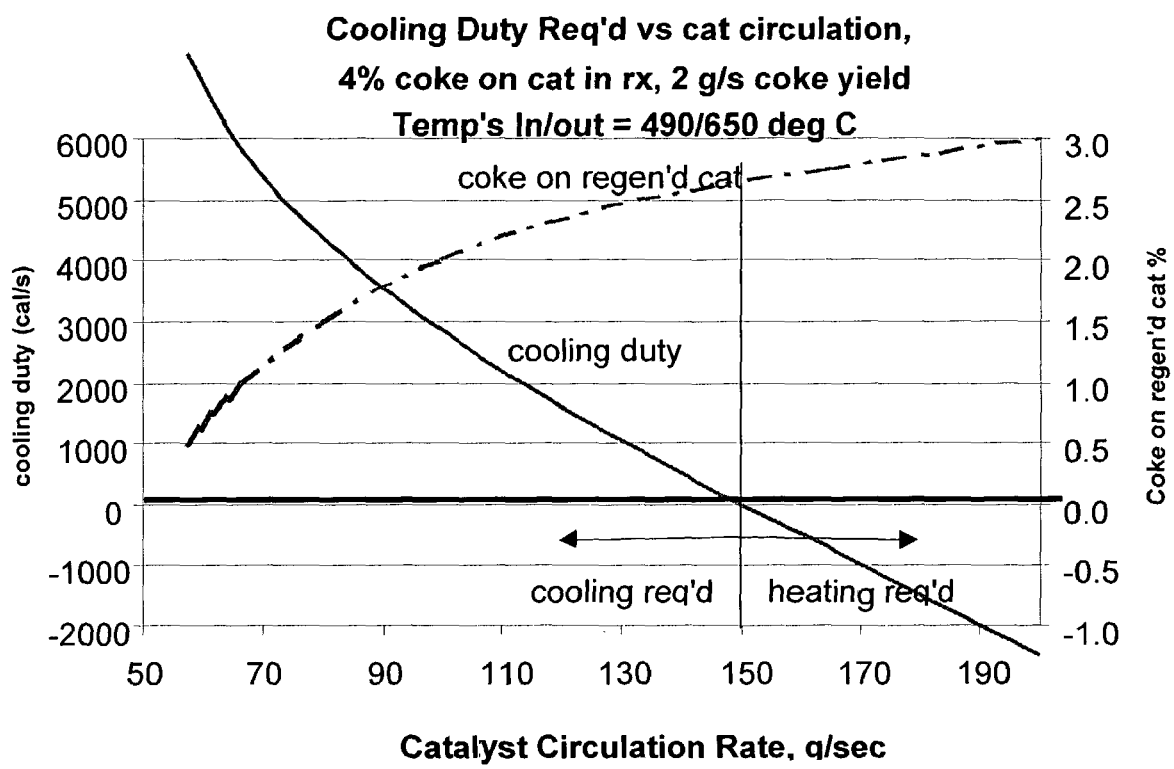
FIGURE

REGENERATION TEMPERATURE CONTROL IN A CATALYTIC REACTION SYSTEM

FIELD OF THE INVENTION

This invention is to a process for controlling catalyst regeneration temperature in a catalytic process incorporating a reactor an regenerator. In particular, the invention is to a process for controlling catalyst regeneration in a system for converting an oxygenate stream to an olefin product using a molecular sieve catalyst.

BACKGROUND OF THE INVENTION

Molecular sieve catalysts have been used to convert oxygenate compounds to olefins. In this conversion process, a carbonaceous material, coke, is deposited on the catalyst. As the coke level builds, the catalyst deactivates. However, the catalyst can be reactivated by burning off the coke. This burning process is generally referred to as regeneration.

U.S. Pat. No. 4,873,390, Lewis, discloses a process for catalytically converting oxygenate to olefins. The process uses a molecular sieve catalyst that has been partially regenerated in order to increase the selectivity to desired olefin products. The preferred catalyst contains silicoaluminophosphate molecular sieve.

U.S. Pat. No. 6,023,005, Lattner, also discloses a process for catalytically converting oxygenate to olefins. This process, however, burns off most, if not all, of the coke deposit on the molecular sieve catalyst. In order to maintain a high selectivity to a desired olefin product, a relatively high average level of coke is maintained on the catalyst in the reactor. The desired level of coke on the catalyst is maintained by circulating a portion of the coked catalyst to the reactor without regenerating it. The regeneration process is shown to include a catalyst cooler.

Vora et al., "Conversion of Natural Gas to Ethylene and Propylene: UOP/HYDRO/MTO Process," *Chemical Engineering of Oil and Gas*, Luzhou, Sichuan, China, July 1997, disclose a process for making olefins from methanol using a SAPO-34 based catalyst. Because of the high heat of reaction and the need to frequently regenerate the catalyst, the process uses a fluidized bed reactor and regenerator. The heat of reaction is removed by steam generation. Because of the fluidized bed conditions and well-mixed catalyst, the temperature in the reactor is almost isothermal. The spent catalyst is sent to the regenerator, where the coke is burned from the catalyst, Steam is generated in the regenerator to remove the exothermic heat resulting from coke burning.

As suggest by Vora et al., heat released during catalyst regeneration in the fluidized bed process of converting oxygenate to olefin is generally quite substantial, since a substantial amount of coke must be removed by reaction with oxygen before the catalyst is considered sufficiently regenerated for reuse. Typically, a means for heat removal (cooling) must be provided to prevent excessive regeneration temperatures, which requires relatively complex and costly equipment. It would, therefore, be highly beneficial to maintain the required degree of coke removal, yet sufficiently control catalyst temperature such that equipment for catalyst cooling could be eliminated. It is especially desirable to eliminate the need to use heat exchange equipment specifically for the purpose of catalyst cooling in the process of making olefin from oxygenate.

SUMMARY OF THE INVENTION

This invention provides a process by which regenerator temperature can be controlled in an oxygenate to olefin reaction system. The process involves circulating catalyst at a rate sufficient to maintain a relatively constant temperature in the regenerator, without having to use a catalyst cooler.

In one embodiment, the invention provides a process for forming olefin product and regenerating coked molecular sieve catalyst. In a particular embodiment, the process comprises contacting an oxygenate stream with a molecular sieve catalyst in a reactor to form an olefin product and a coked catalyst, the coked catalyst having a coke level of at least about 1.5% by weight, based on total weight of the catalyst. The coked catalyst is contacted with an oxygen-containing gas in a regenerator to form a regenerated catalyst having a coke level less than that of the coked catalyst, wherein the coked catalyst enters the regenerator at a temperature less than that of the regenerated catalyst that leaves the regenerator. The regenerated catalyst is circulated to the reactor and the coked catalyst to the regenerator at a rate to maintain a delta coke to delta T ratio of preferably not greater than about 0.015 weight percent per ° C., wherein the delta coke is the level of coke on the coked catalyst minus the level of coke on the regenerated catalyst, and the delta T is the temperature of the regenerated catalyst leaving the regenerator minus the temperature of the coked catalyst entering the regenerator.

The invention is further directed to a process for forming olefin product and regenerating coked molecular sieve catalyst. In one embodiment, the process comprises contacting an oxygenate stream with a molecular sieve catalyst in a reactor to form an olefin product and a coked catalyst, the coked catalyst preferably having a coke level of at least about 1.5% by weight, based on total weight of the catalyst. The coked catalyst is contacted with an oxygen-containing gas in a regenerator to form a regenerated catalyst having a coke level less than that of the coked catalyst, wherein the coked catalyst enters the regenerator at a temperature less than that of the regenerated catalyst that leaves the regenerator. The regenerated catalyst is circulated to the reactor and the coked catalyst to the regenerator at a rate to maintain a delta coke to delta T ratio of not greater than about 0.015 weight percent per ° C., wherein the delta coke is the level of coke on the coked catalyst minus the level of coke on the regenerated catalyst, and the delta T is the temperature of the regenerated catalyst leaving the regenerator minus the temperature of the coked catalyst entering the regenerator.

The invention is also directed to a process for controlling regenerator temperature in a system for forming olefin product from an oxygenate stream. In one embodiment, the process comprises providing the system for forming the olefin product from an oxygenate stream, the system comprising a reactor and regenerator connected via circulation lines. The oxygenate stream is contacted with a molecular sieve catalyst in the reactor at a temperature effective to form an olefin product and a coked catalyst, the coked catalyst preferably having a coke level of from about 4% to about 10% by weight, based on total weight of the catalyst. The coked catalyst is contacted with an oxygen-containing gas in a regenerator to form a regenerated catalyst having a coke level less than that of the coked catalyst. The regenerated catalyst is circulated to the reactor and the coked catalyst to the regenerator via the circulations lines, without passing the regenerated catalyst through a heat removal system, preferably at an average catalyst feedstock exposure index of at least 0.1.

In one embodiment of the invention, the regenerated catalyst leaves the regenerator at a temperate that is at least 50° C. higher than that of the coked catalyst entering the reactor, preferably at a temperate that is at least 75° C. higher than that of the coked catalyst entering the reactor. It is also desirable that the coked catalyst have a coke level of from 2% to 30% by weight, based on total weight of the catalyst, preferably a coke level of from 3% to 20% by weight, based on total weight of the catalyst, more preferably a coke level of from 4% to 10% by weight, based on total weight of the catalyst.

In another embodiment, the regenerated catalyst is circulated to the reactor without passing the regenerated catalyst through a heat removal system. Preferably, the coked catalyst is contacted with the oxygen-containing fluid in the regenerator at an average temperature of from 300° C. to 1,500° C., more preferably at an average temperature of from 400° C. to 1,000° C., and most preferably at an average temperature of from 500° C. to 700° C.

In order to avoid imbalances in catalyst activity or selectivity it is desirable to add the oxygen-containing fluid to the regenerator at a rate at which coke removal in the regenerator is substantially equal to coke deposit in the reactor. In one embodiment, the regenerated catalyst is circulated to the reactor at an average catalyst feedstock exposure index of at least 0.1 preferably at an average catalyst feedstock exposure index of at least 0.5.

In another embodiment of the invention, the oxygenate stream is provided to the reactor in liquid form. Optionally, the oxygenate stream comprises a diluent.

In yet another embodiment, non-reactive solids, which contain no reactive molecular sieve, is circulated with the regenerated and coked molecular sieve catalyst. Preferably, the molecular sieve catalyst has a heat capacity of from 0.05 to 1 cal/g-° C., and the non-reactive solids have a heat capacity of from 0.05 to 1 cal/g-° C.

BRIEF DESCRIPTION OF THE DRAWING

An example of one embodiment of this invention is shown in the attached FIGURE, wherein the FIGURE shows coke level removed from catalyst in a regenerator, and the cooling duty required in the regenerator, as a function of catalyst circulation rate between the regenerator and a reactor.

DETAILED DESCRIPTION OF THE INVENTION

I. Controlling Regenerator Temperature

This invention is directed to controlling regenerator temperature in an oxygenate to olefin process. In the oxygenate to olefin process, oxygenate is contacted with a molecular sieve catalyst in a reactor at a temperature effective to form an olefin product and a coked catalyst. The olefin product is separated from the coked catalyst and at least a portion of the coked catalyst is sent to a regenerator. In the regenerator, the coked catalyst is contacted with an oxygen-containing gas to regenerate the catalyst (i.e., burn off the coke from the catalyst).

Since the coked catalyst entering the regenerator is hot, contacting the coked catalyst with oxygen in the regenerator causes the coke to be burned off the catalyst to form CO, and/or $CO_2$, and water as primary combustion products, leaving behind the regenerated catalyst. The combustion products are separated from the regenerated catalyst, and the regenerated coke is circulated back to the reactor for reuse in the oxygenate to olefin reaction. The regenerated catalyst that is sent back to the reactor can be completely regenerated or partially regenerated. That is, the catalyst sent back to the reactor can have all of the coke removed in the regenerator or only a portion. In a preferred embodiment of this invention, the coke is partially removed from the catalyst in the regenerator.

Because a significant amount of heat can be produced in the regenerator during the regeneration process, at least a portion of the heat must be removed to keep the system from getting too hot. This invention removes heat during the regeneration of the catalyst, using appropriate circulation of catalyst between the reactor and the regenerator. The process of this invention allows the regenerator to be operated so that regenerated catalyst flowing from the regenerator back to the reactor of the oxygenate to olefin process does not require substantial cooling. This means that a heat removal system (e.g., heat exchange equipment) which might conventionally be used to cool the catalyst sent from the regenerator back to the reactor can be substantially reduced in capacity or entirely eliminated.

II. Examples of Catalysts

Any catalyst capable of converting oxygenate to olefin can be used in this invention. Molecular sieve catalysts are preferred. Examples of such catalysts include zeolite as well as non-zeolite molecular sieves, and are of the large, medium or small pore type. Non-limiting examples of these molecular sieves are the small pore molecular sieves, AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG THO, and substituted forms thereof; the medium pore molecular sieves, AFO, AEL, EUO, HEU, FER, MEL, MFI, MTW, MTT, TON, and substituted forms thereof, and the large pore molecular sieves, EMT, FAU, and substituted forms thereof. Other molecular sieves include ANA, BEA, CFI, CLO, DON, GIS, LTL, MER, MOR, MWW and SOD. Non-limiting examples of the preferred molecular sieves, particularly for converting an oxygenate containing feedstock into olefin(s), include AEL, AFY, BEA, CHA, EDI, FAU, FER, GIS, LTA, LTL, MER, MFI, MOR, MTT, MWW, TAM and TON. In one preferred embodiment, the molecular sieve of the invention has an AEI topology or a CHA topology, or a combination thereof, most preferably a CHA topology.

Molecular sieve materials all have 3-dimensional, four-connected framework structure of corner-sharing $TO_4$ tetrahedra, where T is any tetrahedrally coordinated cation. These molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., *Introduction to Zeolite Science and Practice, Second Completely Revised and Expanded Edition*, Volume 137, pages 1-67, Elsevier Science, B.V., Amsterdam, Netherlands (2001).

The small, medium and large pore molecular sieves have from a 4-ring to a 12-ring or greater framework-type. In a preferred embodiment, the molecular sieves have 8-, 10- or 12-ring structures or larger and an average pore size in the range of from about 3 Å to 15 Å. In the most preferred embodiment, the molecular sieves of the invention, preferably silicoaluminophosphate molecular sieves, have 8-rings and an average pore size less than about 5 Å, preferably in the range of from 3 Å to about 5 Å, more preferably from 3 Å to about 4.5 Å, and most preferably from 3.5 Å to about 4.2 Å.

Molecular sieves, particularly zeolitic and zeolitic-type molecular sieves, preferably have a molecular framework of one, preferably two or more corner-sharing [TO$_4$] tetrahedral units, more preferably, two or more [SiO$_4$], [AlO$_4$] and/or [PO$_4$] tetrahedral units, and most preferably [SiO$_4$], [AlO$_4$] and [PO$_4$] tetrahedral units. These silicon, aluminum, and phosphorous based molecular sieves and metal containing silicon, aluminum and phosphorous based molecular sieves have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZNAPSO, EP-A-0 161 489 (CoAPSO), EP-A-0 158 976 (ELAPO, where EL is Co, Fe, Mg, Mn, Ti or Zn), U.S. Pat. No. 4,310,440 (AlPO$_4$), EP-A-0 158 350 (SENAPSO), U.S. Pat. No. 4,973,460 (LiAPSO), U.S. Pat. No. 4,789,535 (LiAPO), U.S. Patent No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326 and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500,651, 4,551,236 and 4,605,492 (TiAPO), U.S. Pat. Nos. 4,824,554, 4,744,970 (CoAPSO), U.S. Pat. No. 4,735,806 (GaAPSO) EP-A-0 293 937 (QAPSO, where Q is framework oxide unit [QO$_2$]), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066 and 5,675,050, all of which are herein fully incorporated by reference.

Other molecular sieves include those described in EP-0 888 187 B1 (microporous crystalline metallophosphates, SAPO$_4$ (UIO-6)), U.S. Pat. No. 6,004,898 (molecular sieve and an alkaline earth metal), U.S. patent application Ser. No. 09/511,943 filed Feb. 24, 2000 (integrated hydrocarbon co-catalyst), PCT WO 01/64340 published Sep. 7, 2001 (thorium containing molecular sieve), and R. Szostak, *Handbook of Molecular Sieves*, Van Nostrand Reinhold, New York, N.Y. (1992), which are all herein fully incorporated by reference.

The more preferred silicon, aluminum and/or phosphorous containing molecular sieves, and aluminum, phosphorous, and optionally silicon, containing molecular sieves include aluminophosphate (ALPO) molecular sieves and silicoaluminophosphate (SAPO) molecular sieves and substituted, preferably metal substituted, ALPO and SAPO molecular sieves. The most preferred molecular sieves are SAPO molecular sieves, and metal substituted SAPO molecular sieves. In an embodiment, the metal is an alkali metal of Group IA of the Periodic Table of Elements, an alkaline earth metal of Group IIA of the Periodic Table of Elements, a rare earth metal of Group IIIB, including the Lanthanides: lanthanum, cerium, praseodymium, neodymium, samarium, europium, gadolinium, terbium, dysprosium, holmium, erbium, thulium, ytterbium and lutetium; and scandium or yttrium of the Periodic Table of Elements, a transition metal of Groups IVB, VB, VIB, VIIB, VIIIB, and IB of the Periodic Table of Elements, or mixtures of any of these metal species. In one preferred embodiment, the metal is selected from the group consisting of Co, Cr, Cu, Fe, Ga, Ge, Mg, Mn, Ni, Sn, Ti, Zn and Zr, and mixtures thereof. In another preferred embodiment, these metal atoms discussed above are inserted into the framework of a molecular sieve through a tetrahedral unit, such as [MeO$_2$], and carry a net charge depending on the valence state of the metal substituent. For example, in one embodiment, when the metal substituent has a valence state of +2, +3, +4, +5, or +6, the net charge of the tetrahedral unit is between −2 and +2.

In one embodiment, the molecular sieve, as described in many of the U.S. patents mentioned above, is represented by the empirical formula, on an anhydrous basis:

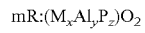

$$mR:(M_xAl_yP_z)O_2$$

wherein R represents at least one templating agent, preferably an organic templating agent; m is the number of moles of R per mole of $(M_xAl_yP_z)O_2$ and m has a value from 0 to 1, preferably 0 to 0.5, and most preferably from 0 to 0.3; x, y, and z represent the mole fraction of Al, P and M as tetrahedral oxides, where M is a metal selected from one of Group IA, IIA, IB, IIIB, IVB, VB, VIB, VIIB, VIIIB and Lanthanide's of the Periodic Table of Elements, preferably M is selected from one of the group consisting of Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01.

In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Non-limiting examples of SAPO and ALPO molecular sieves used in the invention include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44 (U.S. Pat. No. 6,162,415), SAPO-47, SAPO-56, ALPO-5, ALPO-11, ALPO-18, ALPO-31, ALPO-34, ALPO-36, ALPO-37, ALPO-46, and metal containing molecular sieves thereof. The more preferred zeolite-type molecular sieves include one or a combination of SAPO-18, SAPO-34, SAPO-35, SAPO-44, SAPO-56, ALPO-18 and ALPO-34, even more preferably one or a combination of SAPO-18, SAPO-34, ALPO-34 and ALPO-18, and metal containing molecular sieves thereof, and most preferably one or a combination of SAPO-34 and ALPO-18, and metal containing molecular sieves thereof.

In an embodiment, the molecular sieve is an intergrowth material having two or more distinct phases of crystalline structures within one molecular sieve composition. In particular, intergrowth molecular sieves are described in the U.S. patent application Ser. No. 09/924,016 filed Aug. 7, 2001 and PCT WO 98/15496 published Apr. 16, 1998, both of which are herein fully incorporated by reference. In another embodiment, the molecular sieve comprises at least one intergrown phase of AEI and CHA framework-types. For example, SAPO-18, ALPO-18 and RUW-18 have an AEI framework-type, and SAPO-34 has a CHA framework-type.

In one embodiment, the molecular sieves used in the invention are combined with one or more other molecular sieves. In another embodiment, the preferred silicoaluminophosphate or aluminophosphate molecular sieves, or a combination thereof, are combined with one more of the following non-limiting examples of molecular sieves described in the following: Beta (U.S. Pat. No. 3,308,069), ZSM-5 (U.S. Pat. Nos. 3,702,886, 4,797,267 and 5,783,321), ZSM-11 (U.S. Pat. No. 3,709,979), ZSM-12 (U.S. Pat. No. 3,832,449), ZSM-12 and ZSM-38 (U.S. Pat. No. 3,948,758), ZSM-22 (U.S. Pat. No. 5,336,478), ZSM-23 (U.S. Pat. No. 4,076,842), ZSM-34 (U.S. Pat. No. 4,086,186), ZSM-35 (U.S. Pat. No. 4,016,245, ZSM-48 (U.S. Pat. No. 4,397,827), ZSM-58 (U.S. Pat. No. 4,698,217), MCM-1 (U.S. Pat. No. 4,639,358), MCM-2 (U.S. Pat. No. 4,673,559), MCM-3 (U.S. Pat. No. 4,632,811), MCM-4 (U.S. Pat. No. 4,664,897), MCM-5 (U.S. Pat. No. 4,639,357), MCM-9 (U.S. Pat. No. 4,880,611), MCM-10 (U.S. Pat. No. 4,623,527), MCM-14 (U.S. Pat. No. 4,619,818), MCM-22 (U.S. Pat. No. 4,954,325), MCM-41 (U.S. Pat. No. 5,098,684), M-41S (U.S. Pat. No. 5,102,643), MCM-48 (U.S. Pat. No. 5,198,203), MCM-49 (U.S. Pat. No. 5,236,575), MCM-56 (U.S. Pat. No. 5,362,697), ALPO-11 (U.S. Pat. No. 4,310,440), titanium aluminosilicates (TASO), TASO-45 (EP-A-0 229,-295), boron silicates (U.S. Pat. No. 4,254,297), titanium aluminophosphates (TAPO) (U.S. Pat. No. 4,500,651), mixtures of ZSM-5 and ZSM-11 (U.S. Pat. No. 4,229,424), ECR-18 (U.S. Pat. No. 5,278,345), SAPO-34 bound ALPO-5 (U.S. Pat. No. 5,972,203), PCT WO 98/57743 published Dec. 23, 1988 (molecular sieve and Fischer-Tropsch), U.S. Pat. No. 6,300,535 (MFI-bound zeolites), and mesoporous molecular sieves (U.S. Pat. Nos. 6,284,696, 5,098,684, 5,102,643 and 5,108,725), which are all herein fully incorporated by reference.

The molecular sieves are made or formulated into catalysts by combining the synthesized molecular sieves with a binder and/or a matrix material to form a molecular sieve catalyst composition or a formulated molecular sieve catalyst composition. This formulated molecular sieve catalyst composition is formed into useful shape and sized particles by conventional techniques such as spray drying, pelletizing, extrusion, and the like.

There are many different binders that are useful in forming the molecular sieve catalyst composition. Non-limiting examples of binders that are useful alone or in combination include various types of hydrated alumina, silicas, and/or other inorganic oxide sol. One preferred alumina containing sol is aluminum chlorhydrol. The inorganic oxide sol acts like glue binding the synthesized molecular sieves and other materials such as the matrix together, particularly after thermal treatment. Upon heating, the inorganic oxide sol, preferably having a low viscosity, is converted into an inorganic oxide matrix component. For example, an alumina sol will convert to an aluminum oxide matrix following heat treatment.

Aluminum chlorhydrol, a hydroxylated aluminum based sol containing a chloride counter ion, has the general formula of $Al_mO_n(OH)_oCl_p \cdot x(H_2O)$ wherein m is 1 to 20, n is 1 to 8, o is 5 to 40, p is 2 to 15, and x is 0 to 30. In one embodiment, the binder is $Al_{13}O_4(OH)_{24}Cl_7 \cdot 12(H_2O)$ as is described in G. M. Wolterman, et al., Stud. Surf. Sci. and Catal., 76, pages 105-144 (1993), which is herein incorporated by reference. In another embodiment, one or more binders are combined with one or more other non-limiting examples of alumina materials such as aluminum oxyhydroxide, γ-alumina, boehmite, diaspore, and transitional aluminas such as α-alumina, β-alumina, γ-alumina, δ-alumina, ε-alumina, κ-alumina, and ρ-alumina, aluminum trihydroxide, such as gibbsite, bayerite, nordstrandite, doyelite, and mixtures thereof.

In another embodiment, the binders are alumina sols, predominantly comprising aluminum oxide, optionally including some silicon. In yet another embodiment, the binders are peptized alumina made by treating alumina hydrates such as pseudobohemite, with an acid, preferably an acid that does not contain a halogen, to prepare sols or aluminum ion solutions. Non-limiting examples of commercially available colloidal alumina sols include Nalco 8676 available from Nalco Chemical Co., Naperville, Ill., and Nyacol available from The PQ Corporation, Valley Forge, Pa.

The molecular sieve, in a preferred embodiment, is combined with one or more matrix materials. Matrix materials are typically effective in reducing overall catalyst cost, act as thermal sinks assisting in shielding heat from the catalyst composition for example during regeneration, densifying the catalyst composition, increasing catalyst strength such as crush strength and attrition resistance, and to control the rate of conversion in a particular process.

Non-limiting examples of matrix materials include one or more of: rare earth metals, metal oxides including titania, zirconia, magnesia, thoria, beryllia, quartz, silica or sols, and mixtures thereof, for example silica-magnesia, silica-zirconia, silica-titania, silica-alumina and silica-alumina-thoria. In an embodiment, matrix materials are natural clays such as those from the families of montmorillonite and kaolin. These natural clays include sabbentonites and those kaolins known as, for example, Dixie, McNamee, Georgia and Florida clays. Non-limiting examples of other matrix materials include: haloysite, kaolinite, dickite, nacrite, or anauxite. In one embodiment, the matrix material, preferably any of the clays, are subjected to well known modification processes such as calcination and/or acid treatment and/or chemical treatment.

In one preferred embodiment, the matrix material is a clay or a clay-type composition, preferably the clay or clay-type composition having a low iron or titania content, and most preferably the matrix material is kaolin. Kaolin has been found to form a pumpable, high solid content slurry, it has a low fresh surface area, and it packs together easily due to its platelet structure. A preferred average particle size of the matrix material, most preferably kaolin, is from about 0.1 μm to about 0.6 μm with a D90 particle size distribution of less than about 1 μm.

In another embodiment, the weight ratio of the binder to the matrix material used in the formation of the molecular sieve catalyst composition is from 0:1 to 1:15, preferably 1:15 to 1:5, more preferably 1:10 to 1:4, and most preferably 1:6 to 1:5. It has been found that a higher sieve content, lower matrix content, increases the molecular sieve catalyst composition performance, however, lower sieve content, higher matrix material, improves the attrition resistance of the composition.

In another embodiment, the formulated molecular sieve catalyst composition contains from about 1% to about 99%, more preferably from about 5% to about 90%, and most preferably from about 10% to about 80%, by weight of the molecular sieve based on the total weight of the molecular sieve catalyst composition.

In another embodiment, the weight percent of binder in or on the spray dried molecular sieve catalyst composition based on the total weight of the binder, molecular sieve, and matrix material is from about 2% by weight to about 30% by weight, preferably from about 5% by weight to about 20% by weight, and more preferably from about 7% by weight to about 15% by weight.

Once the molecular sieve catalyst composition is formed in a substantially dry or dried state, to further harden and/or activate the formed catalyst composition, a heat treatment such as calcination, at an elevated temperature is usually performed. A conventional calcination environment is air that typically includes a small amount of water vapor. Typical calcination temperatures are in the range from about 400° C. to about 1,000° C., preferably from about 500° C. to about 800° C., and most preferably from about 550° C. to about 700° C., preferably in a calcination environment such as air, nitrogen, helium, flue gas (combustion product lean in oxygen), or any combination thereof.

III. Description of Oxygenate Feedstock

Oxygenate feedstock that can be used as the oxygenate of this invention can be any oxygenate that is capable of forming olefin, particularly ethylene and propylene, upon contacting the olefin forming catalyst. In a preferred embodiment of the invention, the oxygenate feedstock contains one or more oxygenates, more specifically, one or more organic compound(s) containing at least one oxygen atom. In the most preferred embodiment of the process of invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts. Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof. In the most preferred embodiment, the feedstock is selected from one or more of methanol, ethanol, dimethyl ether, diethyl ether or a combination thereof, more preferably methanol and dimethyl ether, and most preferably methanol.

The olefin feed stream, in one embodiment, contains one or more diluent(s), typically used to reduce the concentration of the oxygenate, and are generally non-reactive to the oxygenate or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent is either added directly to the olefin feedstock entering into a reactor or added directly into a reactor, or added with a molecular sieve catalyst composition. In one embodiment, the amount of diluent in the feedstock is in the range of from about 1 to about 99 mole percent based on the total number of moles of the feedstock and diluent, preferably from about 1 to 80 mole percent, more preferably from about 5 to about 50, most preferably from about 5 to about 25. In one embodiment, other hydrocarbons are added to a feedstock either directly or indirectly, and include olefin(s), paraffin(s), aromatic(s) (see for example U.S. Pat. No. 4,677,242, addition of aromatics) or mixtures thereof, preferably propylene, butylene, pentylene, and other hydrocarbons having 4 or more carbon atoms, or mixtures thereof.

IV. Description of Reaction Conditions

According to the reaction process of this invention, oxygenate is contacted with olefin forming catalyst to form an olefin product, particularly ethylene and propylene. The process for converting the oxygenate feedstock is, preferably, a continuous fluidized bed process, and most preferably a continuous high velocity fluidized bed process.

The reaction processes can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. No. 4,076,796, U.S. Pat. No. 6,287,522 (dual riser), and *Fluidization Engineering*, D. Kunii and O. Levenspiel, Robert E. Krieger Publishing Company, New York, N.Y. 1977, which are all herein fully incorporated by reference.

One preferred reactor type is a riser reactor. These types of reactors are generally described in *Riser Reactor, Fluidization and Fluid-Particle Systems*, pages 48 to 59, F. A. Zenz and D. F. Othmo, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In one embodiment of the invention, a fluidized bed process or high velocity fluidized bed process includes a reactor system, catalyst separation system, and a regeneration system. The reactor system preferably is a fluid bed reactor system. In one embodiment, the fluid bed reactor system has a first reaction zone within one or more riser reactors, and a second reaction zone within at least one catalyst separation vessel, preferably comprising one or more cyclones. In one embodiment, at least one riser reactor and catalyst separation device are contained within a single reactor vessel.

An oxygenate stream, preferably containing one or more oxygenates, and optionally one or more diluents, is fed to a fluid bed reactor in which a molecular sieve catalyst composition is introduced. In one embodiment, the molecular sieve catalyst composition is contacted with a liquid or gas, or combination thereof, prior to being introduced to the riser reactor. Preferably, the liquid is water or methanol, and the gas is an inert gas such as nitrogen.

In one embodiment of the invention, the temperature of the regenerator is indirectly controlled by controlling the amount of heat generated in the reactor. One example of controlling the amount of heat generated is by introducing at least a portion of the oxygenate stream into the reactor in liquid form. The greater the liquid content, the less heat generated, since the exothermic heat of reaction of oxygenate conversion is partially absorbed by the endothermic heat of vaporization of the liquid portion of the feed.

In another embodiment, the amount of oxygenate stream that is fed to a reactor system in liquid form is from about 0.1 weight percent to about 85 weight percent, based on the total weight of the oxygenate stream, including any diluent contained therein. Preferably the amount of the oxygenate stream that is fed to the reactor system in liquid form is from about 1 weight percent to about 75 weight percent, more preferably from about 5 weight percent to about 65 weight percent, based on the total weight of the oxygenate stream, including any diluent contained therein.

The liquid and vapor portion of the feed may be the same composition, or may contain varying proportions of the same or different oxygenates and same or different diluents. One particularly effective liquid diluent is water, due to its relatively high heat of vaporization. Other useful diluents are described above. Proper selection of the temperature and pressure of any appropriate oxygenate and/or diluent being fed to the reactor will ensure at least a portion is in the liquid phase as it enters the reactor and/or comes into contact with the catalyst or a vapor portion of the feed and/or diluent.

Optionally, the liquid fraction of the oxygenate stream is split into portions and introduced into the reactor at a multiplicity of locations along its length. This can be done with the oxygenate feed, the diluent, or both. Preferably, this is done with the diluent portion of the feed. Another option is to provide a nozzle which introduces the total liquid fraction of the feed into the inlet zone or reactor in a manner such that the nozzle forms liquid droplets of an appropriate size distribution which, when entrained with the gas and solids introduced to the inlet zone or reactor, vaporize gradually along the length of the reactor. Either of these arrangements or a combination thereof may be used to better control the amount of heat generated. The means of introducing a multiplicity of liquid feed points in a reactor or designing a liquid feed nozzle to control droplet size distribution is well known in the art and is not discussed here.

In another embodiment of the invention, the temperature of the regenerator is controlled by circulating heat absorbing solid particles between the reactor and regenerator. The heat absorbing solid particles are substantially inert solid materials, which do not substantially adversely affect the conversion of the oxygenate to olefin. Preferably, the heat absorbing solid particles contain no molecular sieve as a part of the solid particles. However, the heat absorbing solid particles are, preferably, circulated along with the molecular sieve catalyst between the reactor and the regenerator. Suitable materials for use as heat absorbing solid particles include such materials as metals, metal oxides, and mixtures thereof. Particularly suitable materials are those used as matrices for molecular sieve catalyst formulation, e.g., fillers and binders such as silicas and aluminas, among others, and mixtures thereof. Desirably, the heat absorbing solid particles have a heat capacity of from about 0.05 cal/g-° C. to about 1 cal/g-° C., preferably from about 0.1 cal/g-° C. to about 0.8 cal/g-° C. It is also desirable that the molecular sieve catalyst have a heat capacity of from about 0.05 cal/g-° C. to about 1 cal/g-° C., preferably from about 0.1 cal/g-° C. to about 0.8 cal/g-° C. In another embodiment, the heat absorbing solids are present at a solids to catalyst ratio of from about 0.01:1 to about 10:1, more preferably from about 0.05:1 to about 5:1.

In an embodiment where catalyst and heat absorbing solid particles are circulated between the reactor and regenerator, the catalyst and heat absorbing solid particles are optionally circulated at a rate that is from about 1 to about 200 times that of the total rate of the oxygenate stream input to the reactor. Preferably, the catalyst and heat absorbing solid particles are circulated at a rate that is from about 5 to about 160 times that of the total rate of the oxygenate stream input to the reactor; more preferably from about 10 to about 100 times that of the total rate of the oxygenate stream input to the reactor.

In another embodiment, the molecular sieve catalyst itself is circulated between the reactor and regenerator at a rate of from about 1 to about 100 times that of the total rate of the oxygenate stream input to the reactor. Preferably, the molecular sieve catalyst is circulated at a rate that is from about 5 to about 80 times that of the total rate of the oxygenate stream input to the reactor; more preferably from about 10 to about 50 times that of the total rate of the oxygenate stream input to the reactor.

The oxygenate in the oxygenate feed stream entering the reactor system is preferably converted, partially or fully, in a reactor zone forming an olefin product and a coked catalyst. The olefin product and coked catalyst, as well as any unconverted or unreacted oxygenate, are sent to a catalyst separation vessel where the coked catalyst is separated from the olefin product and the unconverted or unreacted oxygenate.

In a preferred embodiment, cyclones within the separation vessel are used to separate the coked catalyst composition. Gravity effects within the disengaging vessel can also be effective in separating the catalyst. Other processs for separating the catalyst from the gaseous effluent include the use of plates, caps, elbows, and the like.

The average reaction temperature employed in the conversion process, specifically within the reactor, is of from about 250° C. to about 800° C. Preferably the average reaction temperature within the reactor is from about 250° C. to about 750° C.; more preferably, from about 300° C. to about 650° C.; yet more preferably from about 350° C. to about 600° C.; and most preferably from about 400° C. to about 500° C.

The pressure employed in the conversion process, specifically within the reactor, is not critical. The reaction pressure is based on the partial pressure of the feedstock exclusive of any diluent therein. Typically the reaction pressure employed in the process is in the range of from about 0.1 kPaa to about 5 MPaa, preferably from about 5 kPaa to about 1 MPaa, and most preferably from about 20 kPaa to about 500 kPaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. The WHSV is maintained at a level sufficient to keep the catalyst composition in a fluidized state within a reactor.

Typically, the WHSV ranges from about 1 $hr^{-1}$ to about 5000 $hr^{-1}$, preferably from about 2 $hr^{-1}$ to about 3000 $hr^{-1}$, more preferably from about 5 $hr^{-1}$ to about 1500 $hr^{-1}$, and most preferably from about 10 $hr^{-1}$ to about 1000 $hr^{-1}$. In one preferred embodiment, the WHSV is greater than 20 $hr^{-1}$, preferably the WHSV for conversion of a feedstock containing methanol and dimethyl ether is in the range of from about 20 $hr^{-1}$ to about 300 $hr^{-1}$.

The superficial gas velocity (SGV) of the feedstock including diluent and reaction products within the reactor is preferably sufficient to fluidize the molecular sieve catalyst composition within a reaction zone of the reactor. The SGV the process, particularly within the reactor system, more particularly within a riser reactor, is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec.

According to one embodiment, the conversion of oxygenate, particularly the conversion of methanol, is from 90 wt % to 98 wt %. According to another embodiment the conversion of methanol is from 92 wt % to 98 wt %, preferably from 94 wt % to 98 wt %.

According to another embodiment, the conversion of methanol is above 98 wt % to less than 100 wt %. According to another embodiment, the conversion of methanol is from 98.1 wt % to less than 100 wt %; preferably from 98.2 wt % to 99.8 wt %. According to another embodiment, the conversion of methanol is from 98.2 wt % to less than 99.5 wt %; preferably from 98.2 wt % to 99 wt %.

It is desirable to maintain an amount of coke on the catalyst in the reaction vessel to enhance the formation of desired olefin product, particularly ethylene and propylene. It is particularly desirable that the catalyst in the reactor be maintained to contain at least about 1.5 wt % coke, based on total weight of the catalyst. Preferably, the amount of coke maintained on the catalyst in the reactor should be from about 2 wt % to about 30 wt %, based on total weight of the catalyst. More preferably, the amount of coke maintained on the catalyst in the reactor should be from about 3 wt % to about 20 wt %; and most preferably from about 4 wt % to about 10 wt %, based on total weight of the catalyst.

V. Catalyst Separation and Regeneration

After formation of the desired olefin product, the coked catalyst, olefin product and other gases (e.g., unconverted and unreacted feedstock) are sent to a separation vessel or system and the coked catalyst is separated from the olefin product and other gases. The olefin product and other gases are sent to other processing and at least a portion of the coked catalyst is sent to the regenerator to burn off at least a portion of the coke.

In one embodiment of the invention, a portion of the coked molecular sieve catalyst composition is withdrawn from the reactor apparatus and introduced into the regeneration system. The regeneration system comprises a regenerator where the coked catalyst composition is contacted with a regeneration medium, preferably a gas containing oxygen, under general regeneration conditions of temperature, pressure and residence time. Non-limiting examples of the regeneration medium include one or more of oxygen, $O_3$, $SO_3$, $N_2O$, NO, $NO_2$, $N_2O_5$, air, air diluted with nitrogen or carbon dioxide, oxygen and water (U.S. Pat. No. 6,245,703), carbon monoxide and/or hydrogen.

The amount of coke removed from the catalyst in the regenerator depends upon the amount of oxygen added to the regenerator. It is preferred in this invention, that an amount of oxygen be added to the regenerator that is effective to remove only portion of the coke from the coked catalyst.

Of course, the amount of coke on the coked catalyst entering the regenerator will be greater than the amount of coke on the regenerated catalyst leaving the regenerator. Desirably, the amount of coke on the coked catalyst entering the regenerator and the amount of coke on the regenerated catalyst will differ within a range of about 0.5 wt % to about 20 wt %. Preferably, the amount of coke on the coked catalyst entering the regenerator and the amount of coke on the regenerated catalyst will differ within a range of about 1 wt % to about 15 wt %; more preferably, from about 2 wt % to about 10 wt %.

In this invention, the regenerator will operate at a temperature that is higher than that in the reactor. Preferably, the average temperature of the regenerator will be from about 300° C. to about 1,500° C.; more preferably from about 400° C. to about 1,000° C.; and most preferably from about 500° C. to about 700° C. It is also desirable that the regenerated catalyst leave the regenerator at a temperate that is at least about 50° C. higher than that of the coked catalyst entering the reactor; preferably, at least about 75° C. higher than that of the coked catalyst entering the reactor.

VI. Catalyst Circulation

According to this invention, appropriate circulation of catalyst from the reactor to the regenerator and from the regenerator back to the reactor can be used to absorb heat during regeneration. With enough catalyst circulating through the system (i.e., between the reactor and regenerator), excess heat can be removed from the regenerator by the catalyst itself or the catalyst along with heat absorbing solid particles.

In one embodiment of the invention, the coked catalyst is regenerated in a regenerator at a temperature effective to form a regenerated catalyst having a coke level less than that of the coked catalyst. Following regeneration, the regenerated catalyst is removed from the regenerator and circulated back to the reactor. Desirably, the regenerated catalyst is circulated to the reactor and the coked catalyst is circulated to the regenerator at a rate to maintain a delta coke to delta T ratio of not greater than about 0.015 weight percent per ° C. According to this invention, the delta coke is the level of coke on the coked catalyst minus the level of coke on the regenerated catalyst, and the delta T is the temperature of the catalyst leaving the regenerator minus the temperature of the coked catalyst entering the regenerator. Preferably, the regenerated catalyst is circulated to the reactor and the coked catalyst is circulated to the regenerator at a rate to maintain a delta coke to delta T ratio of from about 0.001 to about 0.015 weight percent per ° C., more preferably at a rate to maintain a delta coke to delta T ratio of from about 0.002 to about 0.010 weight percent per ° C.

In another embodiment of the invention, catalyst that has been regenerated is circulated back to the reactor at an average catalyst feedstock exposure (ACFE) index to provide substantially lower propane content in the reaction product compared to a catalyst that is fresh or fully regenerated. As defined herein, the ACFE index is the total weight of oxygenate plus hydrocarbon fed to the reactor divided by the total weight of fresh and regenerated SAPO molecular sieve (i.e., excluding binder, inerts, etc., of the catalyst composition) sent to the reactor, both total weights measured over the same period of time. Fresh catalyst, as used herein, is catalyst that has not been previously used in a reaction process. To determine the ACFE index, the weight of oxygenate and hydrocarbon sent to the reactor and the weight of fresh and regenerated SAPO molecular sieve sent to the reactor should be made over an equivalent time interval. The time interval should be long enough to smooth out fluctuations in catalyst or feedstock rates according to the reactor and regeneration process step selected to allow the system to be viewed as essentially continuous. In the case of reactor systems with substantially constant regeneration, hours or days are usually sufficient.

In this invention, only the molecular sieve in the catalyst sent to the reactor may be used in the determination of ACFE index. The catalyst sent to the reactor, however, can be either fresh or regenerated or a combination of both. Molecular sieve may be circulated to and from the reactor within the reactor apparatus (i.e., via ducts, pipes or annular regions), and which has not been regenerated or does not contain fresh catalyst, is not to be used in the determination of ACFE index.

In this invention, a feed containing an oxygenate, and optionally a hydrocarbon, either separately or mixed with the oxygenate, contacts a catalyst containing a SAPO molecular sieve at process conditions effective to produce olefins in a reactor where the catalyst has an ACFE index of at least about 0.1. The catalyst preferably has an ACFE index of at least about 0.5, more preferably at least about 1.0.

As the rate of catalyst circulation between the reactor and regenerator is set to remove the desired amount of heat from the regenerator, it may be necessary to adjust the amount of oxygen input to the regenerator to obtain a sufficient amount of coke removal from the catalyst. At steady state reaction conditions, it is desirable to remove the same amount of coke in the regenerator that is deposited on the catalyst in the reactor. That is, oxygen-containing fluid should be added to the regenerator at a rate at which coke removal in the regenerator is substantially equal to coke deposit in the reactor. If too little oxygen-containing fluid is added, too little coke will be removed and coke will accumulate over a period of time, eventually causing the catalyst to become inactive. If too much oxygen-containing fluid is added, the result will be that too much coke is taken off, and there will not be enough coke remaining on the catalyst to maintain the desired olefin selectivity. That is, in the oxygenate to olefin process, where it is desired to produce ethylene and/or propylene, selectivity to those products will generally decrease if too much coke is removed from the catalyst that enters the reactor.

VII. Product Recovery and Use

In one embodiment, olefin product and other gases are withdrawn from the reactor and are passed through a recovery system. Any conventional recovery system, technique and/or sequence useful in separating olefin(s) and purifying olefin(s) from other gaseous components can be used in this invention. Examples of recovery systems include one or more or a combination of various separation, fractionation and/or distillation towers, columns, and splitters, and other associated equipment; for example, various condensers, heat exchangers, refrigeration systems or chill trains, compressors, knock-out drums or pots, pumps, and the like.

Non-limiting examples of distillation towers, columns, splitters or trains used alone or in combination include one or more of a demethanizer, preferably a high temperature demethanizer, a deethanizer, a depropanizer, preferably a wet depropanizer, a wash tower often referred to as a caustic wash tower and/or quench tower, absorbers, adsorbers, membranes, ethylene ($C_2$) splitter, propylene ($C_3$) splitter, butene ($C_4$) splitter, and the like.

Various recovery systems useful for recovering predominately olefin(s), preferably prime or light olefin(s) such as ethylene, propylene and/or butene are described in U.S. Pat. No. 5,960,643, U.S. Pat. Nos. 5,019,143, 5,452,581 and 5,082,481, U.S. Pat. No. 5,672,197, U.S. Pat. No. 6,069,288, U.S. Pat. No. 5,904,880, U.S. Pat. No. 5,927,063, and U.S. Pat. No. 6,121,504, U.S. Pat. No. 6,121,503, and U.S. Pat. No. 6,293,998, which are all herein fully incorporated by reference.

Generally accompanying most recovery systems is the production, generation or accumulation of additional products, by-products and/or contaminants along with the preferred prime products. The preferred prime products, the light olefins, such as ethylene and propylene, are typically purified for use in derivative manufacturing processes such as polymerization processes. Therefore, in the most preferred embodiment of the recovery system, the recovery system also includes a purification system. For example, the light olefin(s) produced particularly in a MTO process are passed through a purification system that removes low levels of by-products or contaminants.

Non-limiting examples of contaminants and by-products include generally polar compounds such as water, alcohols, carboxylic acids, ethers, carbon oxides, sulfur compounds such as hydrogen sulfide, carbonyl sulfides and mercaptans, ammonia and other nitrogen compounds, arsine, phosphine and chlorides. Other contaminants or by-products include hydrogen and hydrocarbons such as acetylene, methyl acetylene, propadiene, butadiene and butyne.

Other recovery systems that include purification systems, for example for the purification of olefin(s), are described in *Kirk-Othmer Encyclopedia of Chemical Technology*, 4th Edition, Volume 9, John Wiley & Sons, 1996, pages 249-271 and 894-899, which is herein incorporated by reference. Purification systems are also described in for example, U.S. Pat. No. 6,271,428, U.S. Pat. No. 6,293,999, and U.S. patent application Ser. No. 09/689,363 filed Oct. 20, 2000, which are herein incorporated by reference.

The ethylene and propylene streams produced and recovered according to this invention can be polymerized to form plastic compositions, e.g., polyolefins, particularly polyethylene and polypropylene. Any conventional process for forming polyethylene or polypropylene can be used. Catalytic processes are preferred. Particularly preferred are metallocene, Ziegler/Natta, aluminum oxide and acid catalytic systems. See, for example, U.S. Pat. Nos. 3,258,455; 3,305,538; 3,364,190; 5,892,079; 4,659,685; 4,076,698; 3,645,992; 4,302,565; and 4,243,691, the catalyst and process descriptions of each being expressly incorporated herein by reference. In general, these methods involve contacting the ethylene or propylene product with a polyolefin-forming catalyst at a pressure and temperature effective to form the polyolefin product.

In one embodiment of this invention, the ethylene or propylene product is contacted with a metallocene catalyst to form a polyolefin. Desirably, the polyolefin forming process is carried out at a temperature ranging between about 50° C. and about 320° C. The reaction can be carried out at low, medium or high pressure, being anywhere within the range of about 1 bar to about 3200 bar. For processes carried out in solution, an inert diluent can be used. In this type of operation, it is desirable that the pressure be at a range of from about 10 bar to about 150 bar, and preferably at a temperature range of from about 120° C. to about 250° C. For gas phase processes, it is preferred that the temperature generally be within a range of about 60° C. to 120° C., and that the operating pressure be from about 5 bar to about 50 bar.

In addition to polyolefins, numerous other olefin derivatives may be formed from the ethylene, propylene and $C_4+$ olefins, particularly butylene, separated according to this invention. The olefins separated according to this invention can also be used in the manufacture of such compounds as aldehydes, acids such as $C_2$-$C_{13}$ mono carboxylic acids, alcohols such as $C_2$-$C_{12}$ mono alcohols, esters made from the $C_2$-$C_{12}$ mono carboxylic acids and the $C_2$-$C_{12}$ mono alcohols, linear alpha olefins, vinyl acetate, ethylene dicholoride and vinyl chloride, ethylbenzene, ethylene oxide, cumene, acrolein, allyl chloride, propylene oxide, acrylic acid, ethylene-propylene rubbers, and acrylonitrile, and trimers and dimers of ethylene and propylene. The $C_4+$ olefins, butylene in particular, are particularly suited for the manufacture of aldehydes, acids, alcohols, esters made from $C_5$-$C_{13}$ mono carboxylic acids and $C_5$-$C_{13}$ mono alcohols and linear alpha olefins.

EXAMPLE 1

A continuous pilot plant was used to demonstrate that catalyst circulation could be used to remove heat from the regenerator without having to use a catalyst cooler. The pilot plant operated with a catalyst cooler, and the duty on the cooler could be varied to maintain a constant regenerator temperature. It was found that as the catalyst circulation rate between the regenerator and reactor was increased, the duty required of the cooler to maintain constant regeneration temperature decreased.

The heats of reaction in the combustion process in the regenerator were also calculated. The following was used in the calculation:

Reaction #1 in regenerator: $C + 0.5\ O_2 \rightarrow CO$
Reaction #2 in regenerator: $C + O_2 \rightarrow CO_2$
Reactor exit temperature: 490° C.
Regenerator exit temperature: 650° C.
Coke yield in reactor: 2 g/sec
Coke on catalyst in reactor: 4.0 wt %
Heat capacity of air (used as oxygen-containing medium): 0.255 cal/g ° C.
Heat capacity of catalyst: 0.28 cal/g ° C.
Heat of reaction of #1: −26.4 kcal/g-mol carbon
Heat of reaction of #2: −67.6 kcal/g-mole carbon
Ratio of reaction #1 to reaction #2: 1:1

Using the above, the coke level of the catalyst leaving the regenerator was calculated as a function of the catalyst circulation rate, keeping the coke level on the catalyst from the reactor (i.e., entering the regenerator) at a constant 4 wt %. The result is shown in the FIGURE. As seen from the FIGURE, at a catalyst flow rate of 150 g/sec, the coke on catalyst leaving the regenerator is about 2.6 wt %, and the use of a catalyst cooler is not required. The delta (Δ) coke value is 4−2.7=1.3%. The delta (Δ) temperature value is 650−490=160° C. The ratio of Δ coke:Δ temperature is 0.081.

Having now fully described this invention, it will be appreciated by those skilled in the art that the invention can be performed within a wide range of parameters within what is claimed, without departing from the spirit and scope of the invention.

The invention claimed is:

1. A process for controlling regenerator temperature, the process comprising the steps of:
   a) contacting an oxygenate stream with a molecular sieve catalyst in a reactor to form an olefin product and a coked catalyst;
   b) contacting the coked catalyst with an oxygen-containing fluid in a regenerator to form a regenerated catalyst having a coke level less than that of the coked catalyst; and
   c) controlling temperature and coke levels in the regenerator by circulating the regenerated catalyst to the reactor at an average catalyst feedstock exposure index of at least 0.1 to less than 1.0, wherein the regenerated catalyst is circulated to the reactor and the coked catalyst is circulated to the regenerator at a rate to maintain a delta coke to delta T ratio of from 0.001 to 0.015 weight percent per ° C., wherein the delta coke is the level of coke on the coked catalyst minus the level of coke on the regenerated catalyst, and the delta T is the temperature of the regenerated catalyst leaving the regenerator minus the temperature of coked catalyst entering the regenerator,
   wherein non-reactive solids which contain no reactive molecular sieve are circulated with the regenerated and coked molecular sieve catalyst.

2. The process of claim 1, wherein the regenerated catalyst leaves the regenerator at a temperate that is at least 50° C. higher than that of the coked catalyst entering the reactor.

3. The process of claim 2, wherein the regenerated catalyst leaves the regenerator at a temperate that is at least 75° C. higher than that of the coked catalyst entering the reactor.

4. The process of claim 1, wherein the coked catalyst has a coke level of from 2% to 30% by weight, based on total weight of the catalyst.

5. The process of claim 4, wherein the coked catalyst has a coke level of from 3% to 20% by weight, based on total weight of the catalyst.

6. The process of claim 5, wherein the coked catalyst has a coke level of from 4% to 10% by weight, based on total weight of the catalyst.

7. The process of claim 1, wherein the regenerated catalyst is circulated to the reactor without passing the regenerated catalyst through a heat removal system.

8. The process of claim 2, wherein the coked catalyst is contacted with the oxygen-containing fluid in the regenerator at an average temperature of from 300° C. to 1,500° C.

9. The process of claim 8, wherein the coked catalyst is contacted with the oxygen-containing fluid in the regenerator at an average temperature of from 400° C. to 1,000° C.

10. The process of claim 9, wherein the coked catalyst is contacted with the oxygen-containing fluid in the regenerator at an average temperature of from 500° C. to 700° C.

11. The process of claim 1, wherein an oxygen-containing fluid is added to the regenerator at a rate at which coke removal in the regenerator is substantially equal to coke deposit in the reactor.

12. The process of claim 1, wherein the regenerated catalyst is circulated to the reactor at an average catalyst feedstock exposure index of at least 0.5 to less than 1.0.

13. The process of claim 1, wherein the oxygenate stream comprises a diluent.

14. The process of claim 1, wherein a portion of the oxygenate stream is provided to the reactor in liquid form.

15. The process of claim 14, wherein the oxygenate stream comprises a diluent.

16. The process of claim 1, wherein the molecular sieve catalyst has a heat capacity of from 0.05 to 1 cal/g-° C.

17. The process of claim 1, wherein the non-reactive solids have a heat capacity of from 0.05 to 1 cal/g-° C.

18. A process for forming olefin product and regenerating coked molecular sieve catalyst, the process comprising the steps of:
   a) contacting an oxygen ate steam with a molecular sieve catalyst in a reactor to form an olefin product and a coked catalyst, the coked catalyst having a coke level of at least 1.5% by weight, based on total weight of the catalyst;
   b) contacting the coked catalyst with an oxygen-containing gas in a regenerator to form a regenerated catalyst having a coke level less than that of the coked catalyst, wherein the coked catalyst enters the regenerator at a temperature less than that of the regenerated catalyst that leaves the regenerator; and
   d) controlling temperature and coke levels in the regenerator by circulating the regenerated catalyst to the reactor at an average catalyst feedstock exposure index of at least 0.1 to less than 1.0, wherein the regenerated catalyst is circulated to the reactor and the coked catalyst is circulated to the regenerator at a rate to maintain a delta coke to delta T ratio of from 0.001 to 0.015 weight percent per ° C., wherein the delta coke is the level of coke on the coked catalyst minus the level of coke on the regenerated catalyst, and the delta T is the temperature of the regenerated catalyst leaving the regenerator minus the temperature of coked catalyst entering the regenerator,
   wherein non-reactive solids which contain no reactive molecular sieve are circulated with the regenerated and coked molecular sieve catalyst.

19. The process of claim 18, wherein the regenerated catalyst leaves the regenerator at a temperate that is at least 50° C. higher than that of the coked catalyst entering the reactor.

20. The process of claim 19, wherein the regenerated catalyst leaves the regenerator at a temperate that is at least 75° C. higher than that of the coked catalyst entering the reactor.

21. The process of claim 1, wherein the coked catalyst has a coke level of from 2% to 30% by weight, based on total weight of the catalyst.

22. The process of claim 21, wherein the coked catalyst has a coke level of from 3% to 20% by weight, based on total weight of the catalyst.

23. The process of claim 22, wherein the coked catalyst has a coke level of from 4% to 10% by weight, based on total weight of the catalyst.

24. The process of claim 18, wherein the regenerated catalyst is circulated to the reactor without passing the regenerated catalyst through a heat removal system.

25. The process of claim 18, wherein the average temperature in the regenerator is from 300° C. to 1,500° C.

26. The process of claim 25, wherein the average temperature in the regenerator is from 400° C. to 1,000° C.

27. The process of claim 26, wherein the average temperature in the regenerator is from 500° C. to 700° C.

28. The process of claim 18, wherein an oxygen-containing fluid is added to the regenerator at a rate at which coke removal in the regenerator is substantially equal to coke deposit in the reactor.

29. The process of claim 18, wherein the regenerated catalyst is circulated to the reactor at an average catalyst feed stock exposure index of at least 0.5 to less than 1.0.

30. The process of claim 18, wherein the oxygenate stream comprises a diluent.

31. The process of claim 18, wherein a portion of the oxygenate stream is provided to the reactor in liquid form.

32. The process of claim 31, wherein the oxygenate stream comprises a diluent.

33. The process of claim 18, wherein the molecular sieve catalyst has a heat capacity of from 0.05 to 1 cal/g-° C.

34. The process of claim 18, wherein the non-reactive solids have a heat capacity of from 0.05 to 1 cal/g-° C.

35. A process for controlling regenerator temperature in a system for forming olefin product from an oxygenate stream, the process comprising the steps of:

a) providing the system for forming the olefin product from an oxygenate stream, the system comprising a reactor and regenerator connected via circulation lines;

b) contacting the oxygenate stream with a molecular sieve catalyst in the reactor at a temperature effective to form an olefin product and a coked catalyst, the coked catalyst having a coke level of from 4 wt % to 10 wt %, based on total weight of the catalyst;

c) contacting the coked catalyst with an oxygen-containing gas in a regenerator to form a regenerated catalyst having a coke level less than that of the coked catalyst; and d) controlling temperature and coke levels in the regenerator by circulating the regenerated catalyst to the reactor and the coked catalyst to the regenerator via the circulations lines, without passing the regenerated catalyst through a heat removal system, at an average catalyst feedstock exposure index of at least 0.1 to less than 1.0, wherein the regenerated catalyst is circulated to the reactor and the coked catalyst is circulated to the regenerator at a rate to maintain a delta coke to delta T ratio of from 0.001 to 0.015 weight percent per ° C., wherein the delta coke is die level of coke on the coked catalyst minus the level of coke on the regenerated catalyst, and the delta T is the temperature of the regenerated catalyst leaving the regenerator minus the temperature of coked catalyst entering the regenerator, wherein non-reactive solids which contain no reactive molecular sieve are circulated with the regenerated and coked molecular sieve catalyst.

36. The process of claim 35, wherein the regenerated catalyst is circulated to the reactor at au average catalyst feedstock exposure index of at least 0.5 to less than 1.0.

37. The process of claim 35, wherein the oxygenate stream comprises a diluent.

38. The process of claim 35, wherein a portion of the oxygenate stream is provided to the reactor in liquid form.

39. The process of claim 38, wherein the oxygenate stream comprises a diluent.

40. The process of claim 35, wherein the molecular sieve catalyst has a heat capacity of from 0.05 to 1 cal/g-° C.

41. The process of claim 35, wherein the non-reactive solids have a heat capacity of from 0.05 to 1 cal/g-° C.

* * * * *